United States Patent [19]

Carmosin et al.

[11] Patent Number: 5,543,530

[45] Date of Patent: Aug. 6, 1996

[54] 4-ARYLISOINDOLE ANALGESICS

[75] Inventors: Richard J. Carmosin, Quakertown; John R. Carson, Norristown; Philip Pitis, North Wales; Robert B. Raffa, Norristown, all of Pa.

[73] Assignee: Ortho Pharmaceutical Corporation, Raritan, N.J.

[21] Appl. No.: 173,326

[22] Filed: Dec. 23, 1993

[51] Int. Cl.$^6$ .................. C07D 401/04; C07D 409/04; C07D 209/44; A61K 31/44; A61K 31/40
[52] U.S. Cl. .................. 548/452; 548/466; 546/277.1
[58] Field of Search .................. 548/452, 466; 514/415, 342, 414; 546/273

[56] References Cited

U.S. PATENT DOCUMENTS

| | | | |
|---|---|---|---|
| 4,042,707 | 8/1977 | Ripka | 424/274 |
| 4,689,329 | 8/1987 | Carmosin et al. | 514/299 |
| 5,216,018 | 6/1993 | Ciganek | 514/416 |

FOREIGN PATENT DOCUMENTS

WO94/22823  10/1994  European Pat. Off. .

*Primary Examiner*—David B. Springer
*Attorney, Agent, or Firm*—John W. Harbour

[57] ABSTRACT

The 4-arylisoindoles of the following formula are effective analgesics:

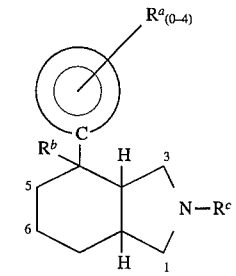

including the purified stereoisomers and pharmaceutically acceptable salts thereof, wherein

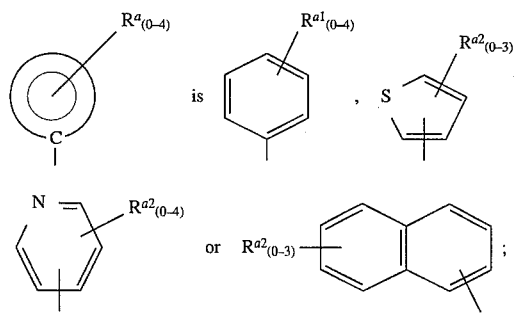

$R^b$ is hydroxy or $C_{1-5}$ alkylcarbonyloxy.

16 Claims, No Drawings

4-ARYLISOINDOLE ANALGESICS

The present invention relates to analgesics. More particularly, the present invention relates to 4-aryloctahydro-1H-isoindoles having analgesic activity.

BACKGROUND OF THE INVENTION

Analgesics used today in clinical practice suffer either from limited efficacy, limiting side effects or both. The non-steriodal antiinflammatory agents such as aspirin and ibuprofen fail to treat severe pain and cause gastrointestinal side effects. The opiates (morphine, codeine or meperidine) can treat more severe pain, but are subject to addiction liability and cause constipation and respiratory depression.

French Patent 8915407, to Rorer-Rhone Polenc, discloses the compound:

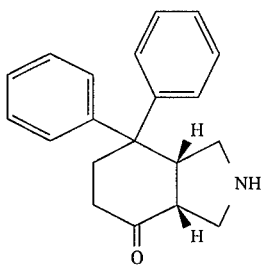

No biological utility is taught.

Eur. Pat. No. 430 771, to Rhone Polenc, discloses the compound:

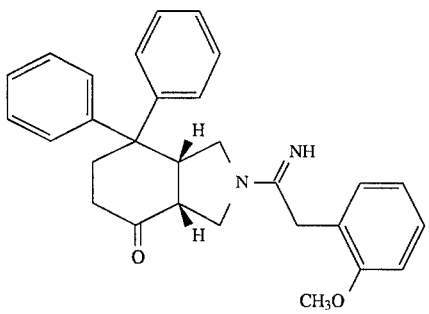

The biological utility is disclosed as a Substance P antagonist.

Ciba-Giegy has publicly disclosed the compound:

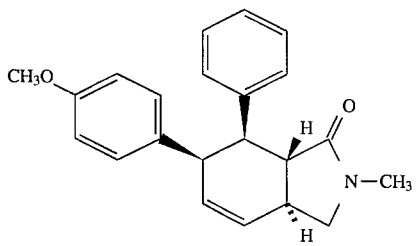

However, no biological activity was taught for this compound and its suitability for use as an analgesic is unknown.

U.S. Pat. No. 5,216,018, to Ciganek discloses isoindoles of the formula:

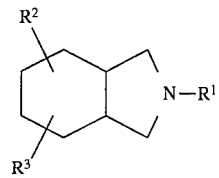

wherein $R^2$ and $R^3$ are disclosed among many other substituents to be independently phenyl. These compounds are disclosed as useful to treat physiological or drug induced psychosis and as antidyskinetic agents.

SUMMARY OF THE INVENTION

The present invention provides novel octahydro-1H-isoindoles having analgesic activity of the formula:

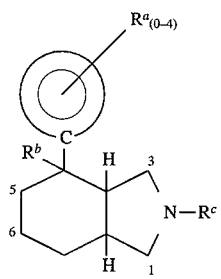

including the purified stereoisomers and pharmaceutically acceptable salts thereof, wherein

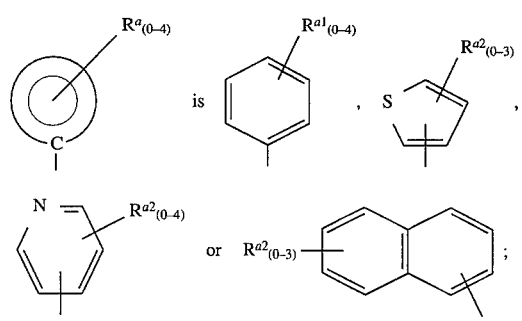

$R^{a1}$ is selected from the group consisting of hydrogen, halogen, $C_{1-4}$alkyl, substituted $C_{1-4}$alkyl (wherein the substituent is $C_{1-4}$alkoxy, hydroxy or perhalo), $C_{1-4}$alkoxy, substituted $C_{1-4}$alkoxy (wherein the substituent is perfluoro), $C_{1-4}$alkylthio, cyano, di$C_{1-4}$alkylamino, $C_{1-4}$alkylsulfonyl, $C_{1-4}$alkylsulfinyl, phenyl, phenylthio and carboxy;

$R^{a2}$ is selected from the group consisting of halogen or $C_{1-4}$alkyl;

$R^b$ is hydroxy or $C_{1-5}$ alkylcarbonyloxy;

$R^c$ is selected from the group consisting of hydrogen, $C_{1-4}$alkyl, substituted $C_{1-4}$alkyl (wherein the substituent is one or two phenyl groups or di$C_{1-4}$alkylamino), $C_{1-4}$alkenyl and benzyl.

DETAILED DESCRIPTION OF THE INVENTION

The compounds of Formula I can be divided into 4 diastereomers

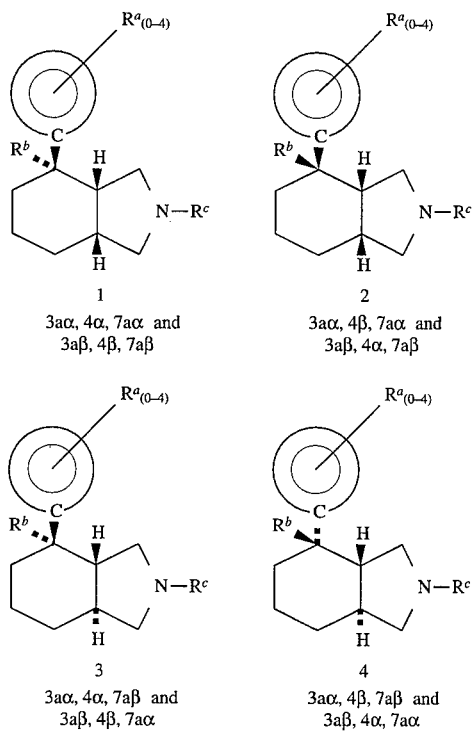

1
3aα, 4α, 7aα and
3aβ, 4β, 7aβ

2
3aα, 4β, 7aα and
3aβ, 4α, 7aβ

3
3aα, 4α, 7aβ and
3aβ, 4β, 7aα

4
3aα, 4β, 7aβ and
3aβ, 4α, 7aα where stereochemistry at the 4-position refers to the aryl substituent and $R^a$, $R^b$ and $R^c$ are as defined above. Unless specifically indicated otherwise, the structures herein represent the depicted stereoisomer as a racemic mixture.

The manufacture of compounds of the Formula (I) may be carried out in a two-stage synthesis scheme. The objective of one stage is to produce the desired stereoisomer of a core 3a,7a-octahydro-1H-isoindole. The other synthetic stage is to substitute the core isoindole with the appropriate substituents, namely aryl-$R^a$, $R^b$ and $R^c$ as defined above. Of course persons skilled in the art will realize that the two objectives are not always seperable. In the first scenario which produces diastereomers 1 and 2, $R^b$ is introduced after the core isoindole formation. With regard to $R^a$ and $R^c$ in the first scenario, they may be introduced either during ring formation or modified after. The second scenario $R^a$ or a chemically modifiable derivative thereof is incorporated into the starting material and $R^b$ is added in the second part of the synthesis. In this scenaio as in the first $R^c$ can either be added in the core producing steps or modified after ring formation.

Flow sheets AA and AB illustrate the synthesis of diastereomers of Formula (1). The instant invention anticipates biological activity for all diastereomers and for their corresponding pure enantiomers. The flow sheets illustrate the case where aryl is phenyl and by analogy naphthyl. The following is a description of the chemistry employed in each suggested procedure.

AA: The synthesis of diastereomers 1 and 2

Diastereomers 1 and 2 may be prepared from commonly available starting materials. The N-(trimethylsilylmethyl)aminomethyl ether derivatives AA3 are produced by a literature procedure (Hosomi, et al. *Chemistry Letters* 1984, 1117–1120). This is a two step synthesis which employs commercially available primary amines AA1 and chloromethyltrimethylsilane in the first step and formaldehyde with an alcohol in the second step. The preferred alcohols are butanol or methanol. Derivative AA3 is treated with 2-cyclohex-2-enone in a suitable solvent at room temperature to reflux, with an amount of trifluoroacetic acid, to give the 2-substituted 3aα, 7aα-octahydoisoindol-4-one derivative AA4. Suitable solvents are methylene chloride, chloroform, tetrachloromethane, benzene, ether and THF. Derivative AA4 can be treated with an organometallic derivative AA5, such as phenyllithium in an inert solvent, such as THF or ether at 0° C. to room temperature for about 1–4 h to give the 4-β-phenyl-3aα, 7aα-octahydroisoindol-4-ol derivative AA6. This derivative corresponds to diastereomer 1 of Formula (1).

Diastereomer 2 may be prepared by treating derivative AA6 with 2N $H_2SO_4$ at 80° C. to give the 4-α-phenyl-3aα, 7aαc-octahydroisoindol-4-ol derivative AA7.

To obtain the pyridine and thiophene derivatives of diastereomers 1 and 2, derivative AA4 is treated with a lithiated pyridine or thiophene derivative AA5. Although they are not commercially available, these derivatives may be prepared by transmetallation of the appropriate heterocyclic halide with an alkyllithium reagent such as n- butyllithium or LDA to give the desired organometallic reagent. The reaction conditions for the production of AA6 and AA7 with pyridine and thiophene derivatives AA5 are comparable to the conditions discussed in the synthesis of the phenyl derivatives.

SCHEME AA

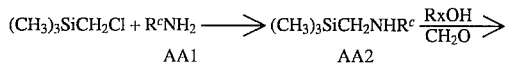

AA1  AA2

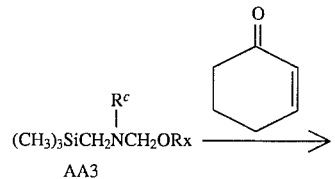

AA3

-continued
SCHEME AA

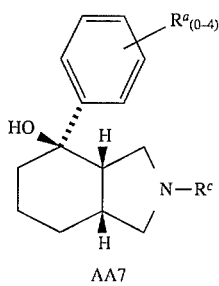

AA7

AB: The synthesis of diastereomers 3 and 4.

Diastereomers 3 and 4 may be prepared from commonly available starting materials which include trans-1-phenyl-1,3-butadienes which are substituted with $R^a$, fumaric acid esters and primary amines. The description herein using the phenyl bearing trans-buta-1,3-diene is for exemplification only. Referring to Flow Sheet AB, trans-1-phenyl-1,3-butadiene AB1 and fumaric acid ester AB2 (where Ry is $C_{1-4}$alkyl) are reacted in an intermolecular Diels-Alder reaction to produce derivative AB3 as a mixture of diastereomeric diesters. The Diels-Alder reaction may be carried out adding the diene AB1 and the dienophile AB2 to an organic solvent and optionally heating or adding a Lewis acid catalyst or pressurizing the reactor. Suitable solvents generally include toluene, xylene, dichlorobenzene, ether, dichloromethane, tetrachloromethane, n-hexane, benzene, ethylene glycol or water. Of course, where heat is to be applied, then a high boiling solvent is desireable. Suitable high boiling organic solvents boil in a temperature range between 80° and 250° C. The reaction might also be carried out with a lower boiling solvent in a pressure apparatus if desired. Suitable Lewis acid catalysts include, aluminum chloride, stannic chloride or boron trifluoride. Preferably the reaction is carried out in a temperature range between room temperature and 180° C. under normal pressure. The diester derivative AB3 may be separated in pure diastereomers via routine purification methods which include column chromatography and recrystallization, but for purposes of this flow scheme this separation is unnecessary. Derivative AB3 may be hydrogenated or subjected to hydride reduction conditions to give the diol derivative AB4 as a mixture of diastereomers. The hydrogenation may be carried out over Raney nickel or over a noble metal, such as, palladium, platinum or rhodium, with or without heat and at pressures from atmospheric to 1000 psi. The hydride reduction may be carried out with a reducing agent in a suitable solvent. Suitable reducing agents include lithium aluminum hydride (LAH) and sodium diethylaluminum hydride. Preferred solvents for use with the named reducing agents are the ethereal solvents. Derivative AB5 may be activated by replacing the hydroxy groups with a leaving group, $Z^b$, such as, iodide, mesylate (methanesulfonate), tosylate (p-toluenesulfonate) or trifluoromethanesulfonate, to produce activated diol derivative AB6 as a mixture of diastereomers. The hydroxyl moieties may be converted to a methanesulfonate group by treating with methanesulfonyl chloride in the presence of triethylamine. A suitable solvent, e.g., dichloromethane, is employed and the reaction is carried out at reduced temperatures. The iodide may be obtained directly from diol AB5 by common methods known to the art, for example, by treatment of the hydroxyl group with methyl triphenoxyphosphonium iodide in a suitable solvent, such as, dimethylformamide, at reduced or ambient temperatures. The hydroxyl group may be converted into the reactive trifluoromethanesulfonate (triflate) group by treatment with trifluoromethanesulfonic (triflic) anhydride in the presence of a hindered, non-nucleophilic base, such as, 2,6-lutidine, 2,4,6-collidine, or 2,6-di-t-butyl-4-methylpyridine, in a suitable solvent, such as, dichloromethane, at reduced temperatures to generate the triflate activating group.

Treatment of the activated diol AB6 with a primary amine derivative AB7 gives the 4-aryl-2-substituted isoindole derivative AB8, as a mixture of diastereomers. In general, the conversion is carried out by simply adding the primary amine AB7 to the activated diol AD6 in a suitable solvent at reduced temperature or ambient temperature. Suitable solvents include acetonitrile, alcohols, DMF or dichloromethane. Conversion of the isoindole derivative AB8 to the delta-4,5-isoindole derivative AB9 may be accomplished by isomerizing the double bond. This isomerization may be performed using strong bases such as n-BuLi, sodium and potassium amide with inert organic solvents. Preferably, the isomerization is performed using potassium-t-butoxide and THF.

The delta-4,5-isoindole derivative AB8 may be oxidized to the corresponding epoxide-N-oxide derivative, AB9, which is isolated and used as a mixture of diastereomers. Reagents for oxidation include peroxyacids m-chloroperbenzoic acid, peroxyacetic acid and monoperthalic acid in their traditional solvents. Preferably the oxidation is accomplished using m-chloroperbenzoic acid in chloroform. The epoxide derivative AB9 is directly treated with a hydride source in a suitable solvent to give a mixture of diastereomers AB10 and AB11. Examples of suitable hydride sources include: lithium aluminum hydride, sodium diethylaluminum hydride or "Red-Al". The reductions may be carried out in their traditional solvents such as THF or. ether at 0° C. to reflux for 1–10 h. The resulting mixture of diasteromers may be purified to give the pure diastereomers AB10 and AB11 which correspond to diastereomers 3 and 4 of the invention, respectively.

Diastereomer AB 10 may be converted to diastereomer AB 11 by using the aforemetioned epimerization procedure described for the conversion of AA6 to AA7.

SCHEME AB

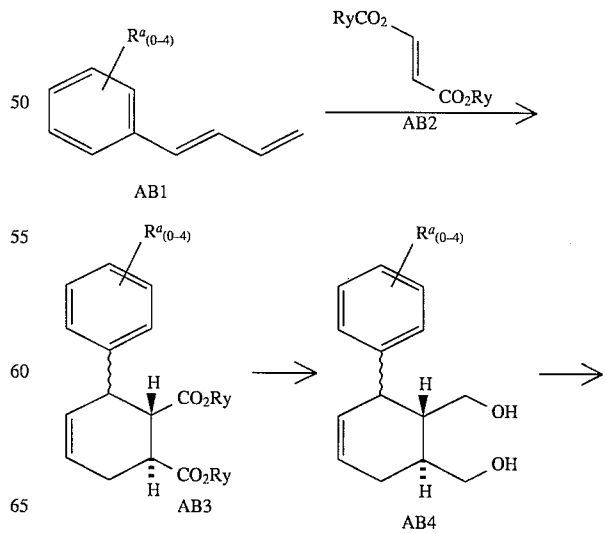

7
-continued
SCHEME AB

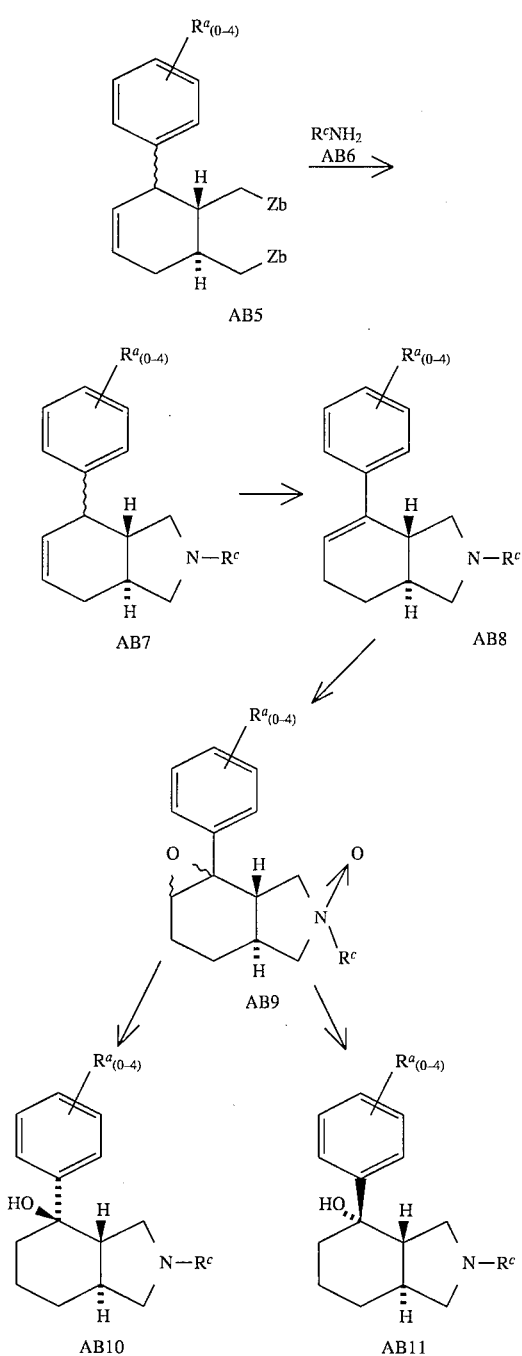

AC: Synthesis of enantiomers of diastereomers 1 and 2

Pure enantiomers of diastereomers 1 and 2 can be prepared by employing a chiral auxiliary as illustrated in Flow Scheme AC. The N-(trimethylsilylmethyl)aminomethyl ether derivatives AC3 are produced by literature procedures (Hosomi, et al. *Chemistry Letters* 1984, 1117–1120). This is a two step synthesis which employs commercially available enantiomerically pure primary amines AC1 and chloromethyltrimethylsilane in the first step and formaldehyde with an alcohol (preferably butanol or methanol). Derivative AC3 is treated with 2-cyclohex-2-enone and a trace of TFA in methylene choloride at reflux to give the 2-substituted 3aα, 7aα-octahydoisoindol- 4-one derivative AC4. AC4 can be treated with an organometallic agent AC5, such as phenyllithium in an inert solvent such as THF or ether at 0° C. to room temperature for about 1–4 h to give the 4-α-phenyl-2-substituted-3aα, 7aα-octahydroisoindol-4-ol derivative as a mixture of diastereomers, AC6 and AC7. This mixture may be separated by routine chromatography and crystallization techniques to give the pure stereoisomer, where the relative positions of the substituents on carbons 4, 3a and 7a are as shown. The pure diastereomer AC7 (AC6 may also be used with comparable reaction conditions, but only one is illustrated) can be treated with an alkyl triflate to give the quarternary isoindole derivative AC8. Suitable solvents for this transformation are ethyl acetate, methylene chloride, THF and chloroform. The chiral auxiliary is removed from AC8 by hydrogenolysis gives the pure enantiomer AC9. Suitable hydrogenolysis conditions include ammonium formate with palladium black, a hydrogen atmosphere (1–20 atm) with an appropriate catalyst such as palladium on carbon. Derivative AC9 is a pure enantiomer which corresponds to diastereomer 1 of Formula (1).

The pure enantiomers of diastereomer 2 may be prepared by treating derivative AC9 with 2N $H_2SO_4$ to give the 4-α-phenyl-3aα, 7aα-octahydroisoindol- 4-ol derivative AC10. This derivative corresponds to diastereomer 2 of Formula (1).

To obtain the pyridine and thiophene compounds, derivative AC4 is treated with a lithiated pyridine or thiophene derivative AC5. The reaction conditions for the production of AC6 with pyridine and thiophene derivatives AC5 are comparable to the reaction conditions discussed in the synthesis of the phenyl derivatives.

SCHEME AC

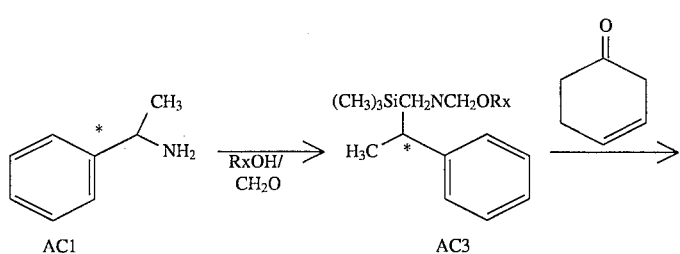

-continued
SCHEME AC

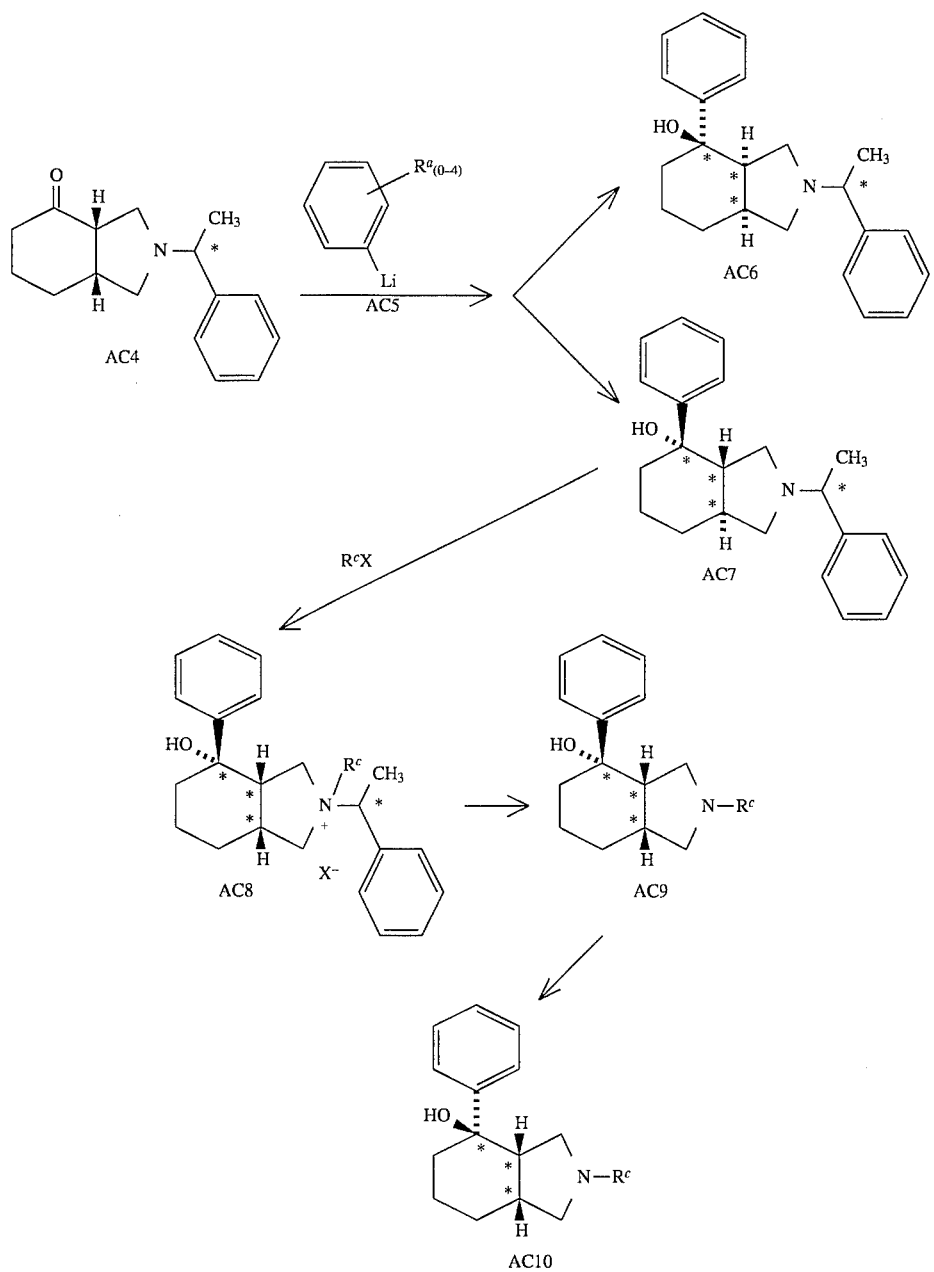

If in the operation of Flow Sheets AA through AC, at the stage of introduction of $R^c$, a chiral auxiliary is similarly employed, diastereomers will be produced which can be, in like manner, converted to the desired enantiomers. Alternatively, by classical resolution techniques diastereomers 1 through 4 can be reacted with chiral acids, such as, (+) or (−) ditoluoyltartaric acid, or (+) or (−) camphorsulfonic acid. Separation of the resultant diastereomeric mixture and subsequent reconversion to the base will produce the desired enantiomers.

The starting materials for all compounds of the invention may be synthesized by methods know to the art or commercially purchased. With regard to Scheme AA, primary amine derivatives AA 1, are commercially available when $R^c$ is selected from $C_{1-4}$ alkyl, substituted alkyl (where the substituent is one or more pheny or dialkylamino groups), $C_{1-4}$ alkenyl, $C_{1-3}$ aralkyl or substituted aralkyl (where the substituent is one or more of $C_{1-4}$ alkyl, $C_{1-4}$ alkoxy or dialkylamino). The phenyl derivative AA5. may be purchased in the case where $R^{a1}$ is hydrogen. When $R^{a1}$ is selected from the group consisting of halogen, $C_{1-4}$alkyl, substituted $C_{1-4}$alkyl (wherein the substituent is $C_{1-4}$alkoxy, or perhalo), $C_{1-4}$alkoxy, substituted $C_{1-4}$alkoxy (wherein the substituent is perfluoro), $C_{1-4}$alkylthio, di$C_{1-4}$alkylamino, $C_{1-4}$alkylsulfonyl, $C_{1-4}$alkylsulfinyl, phenyl, phenylthio and carboxy, derivatives AA5 must be prepared. One may do so by treating the corresponding halo derivatives with n-butyllithium from 0° C. to reflux in a suitable solvent such as ether or THF for 30 min to 6 h. The required haloaryl derivatives are known to the literature. The pyridyl and the thiophene compounds of the invention are produced using an AA5 derivative where the phenyl group is replaced with the appropriate heterocycle. The lithiated heterocyclic derivatives where $R^{a2}$ is hydrogen, halogen or $C_{1-4}$alkyl, may be produced in the manner described above for derivative AA5 where $R^{a1}$ is other than hydrogen.

Derivative AB1 is the starting material for Scheme AB. In the case where $R^{a1}$ hydrogen the derivative is commercially available. When $R^{a1}$ is selected from $C_{1-4}$alkyl, substituted $C_{1-4}$alkyl (wherein the substituent is $C_{1-4}$ alkoxy or perhalo), $C_{1-4}$alkoxy, substituted $C_{1-4}$alkoxy (wherein the substituent is pefluoro), $C_{1-4}$alkylthio, di$C_{1-4}$alkylamino, phenyl and phenylthio, derivative AB1 may be synthesized using a Wittig, a Knoevenagel or a Perkin Condensation. In the Wittig reaction, optionally substituted allyltriphenylphosphonium halide is reacted with optionally substituted benzaldehyde in the presence of a base and in a suitable solvent from 50° C. to room temperature, Effective bases include potassium t-butoxide, n-butyllithium and sodiumhexamethyldisilazide and useful solvents are inert solvents such as THF. The substituted benzaldehydes for the aforementioned substitutents are all know to the art. The naphthyl derivatives of AB1 may be obtained in a similar manner to the phenyl derivatives of AB1. The pyridyl and thiophene derivatives of AB1 where $R^{a2}$ is selected from hydrogen, halogen or $C_{1-4}$alkyl can be prepared. As above the Wittig reaction is employed using the known appropriately substituted heterocyclic aldehyde derivatives.

With regard to Scheme AC the chiral α-phenethylamine derivative A(C1 is commercially available. Examples of suitable chiral amines include (+) or (−)-α-methylphenethylamine, (+) or (−)-α-methyl-p-chlorophenethylamine and (+) or (−)-α-1-naphthylethylamine.

Certain compounds of formula I are best prepared by transformation of one $R^a$ substituent to another. In the case of cyano, this $R^{a1}$ substituent may be obtained by employing Br as a precursor substituent on the octahydro-1H-isoindole. The bromine precursor substituent is replaced with cyano by treatment with sodium cyanide or cuprous cyanide in an inert solvent at elevated temperatures over a Pd(0) catalyst. In the case of the $C_{1-4}$ alkylsulfonyl, these substituents may be obtained by oxidizing a $C_{1-4}$alkylthio precursor substituent on an octahydro-1H-isoindole using hydrogen peroxide in acetic acid, potassium permanganate in water, nitric acid, sodium perborate or meta-chloroperbenzoic acid in halocarbon. In the case of the $C_{1-4}$alkylsulfinyl, these substituents may be obtained by oxidizing a $C_{1-4}$alkylthio precursor substituent on octahydro or hexahydro-1H-isoindole using sodium periodate in water or meta-chloroperbenzoic acid in a halocarbon solvent. In the case of carboxy, this substituent may be obtained by hydrolyzing a cyano precursor substituent on octahydro-1H-isoindole by saponification with sodium hydroxide.

To change the substituent $R^b$ from hydroxyl to $C_{1-5}$alkylcarbonyloxy one may employ acyl halides in inert solvents at from 20° to 30° C. for 1–4 in the presence of an organic base such as triethylamine. Suitable acetyl halides include acetyl chloride, propionyl chloride and butyryl chloride, acceptable solvents include chloroform, methylene chloride, THF and ethyl acetate.

To vary the $R^c$ substituents, one may employ the benzyl substituted octahydro-1H-isoindole. The benzyl group on nitrogen may removed by catalytic debenzylation over a palladium catalyst to give the NH compound. The $R^c$ group is then attached to nitrogen either by alkylation or reductive alkylation. In the case of alkylation, an $R^cX$ reagent is employed where X is a leaving group as discussed in connection with Flow Sheet AC above. The alkylation is carded out in a suitable solvent at elevated temperature or ambient temperature with a suitable base, such as: potassium carbonate, sodium bicarbonate or diisopropylethylamine. Suitable solvents include acetonitrile, alcohols, DMF or dichloromethane. In the case of reductive alkylation the NH compound is reacted with a carbonyl compound and a hydrogen source. The hydrogen source may include hydrogen over a palladium or platinum catalyst or $NaBH_3CN$ or formic acid at elevated temperatures. Where the carbonyl compound is formaldehyde, then $R^c$ is methyl; acetaldehyde, then $R^c$ is ethyl; benzaldehyde, then $R^c$ is benzyl; and acetone, then $R^c$ is isopropyl.

Preferred $R^{a1}$ are selected from the group consisting of bromine, chlorine, fluorine, methyl, ethyl, n-propyl, i-propyl, t-butyl, methoxymethyl, ethoxyethyl, hydroxymethyl, hydroxyethyl, hydroxypropyl, trifluoromethyl, trichloromethyl, methoxy, ethoxy, t-butoxy, trifluoromethoxy, methylthio, ethylthio, n-propylthio, cyano, dimethylamino, diethylamino, methylethylamino, methylsulfonyl, ethylsulfonyl, n-propylsulfonyl, methylsulfinyl, ethylsulfinyl, n-propylsulfinyl, phenyl, phenylthio and carboxy.

Preferred $R^{a2}$ are selected from the group consisting of bromine, chlorine, fluorine, methyl, ethyl, n-propyl, i-propyl or t-butyl.

Preferred $R^b$ are selected from the group consisting of hydroxy and ethylcarbonyloxy.

Preferred $R^c$ are selected from the group consisting of hydrogen, methyl, ethyl, n-propyl, i-propyl, t-butyl, dimethylaminomethyl, dimethylaminoethyl, dimethylaminopropyl, diethylaminomethyl, diethylaminoethyl and allyl.

Preferred compounds of Formula (I) above, incude:

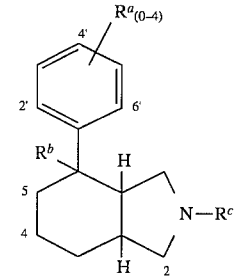

wherein $R^a$, $R^b$ and $R^c$ are simultaneously selected from the group consisting of the groups:

| $R^a$ | $R^b$ | $R^c$ |
|---|---|---|
| 4'-F | OH | Me, |
| 3'-methoxy | OH | Me, |
| 3'-methoxy | OH | H, |
| 3'-$CF_3$ | OH | Me, |
| 3'-methoxy | OH | H, |
| 2',3'-dimethoxy | OH | Me, |
| 3',4'-dichloro | OH | Me, |
| — | OH | Me, |
| 4'-$CF_3$ | OH | Me, |
| 3'-$CF_3$ | OH | n-butyl, |
| 4'-Cl | OH | Me, |
| 2'-Cl | OH | Me, |
| 2',5'-dichloro | OH | Me, |
| 4'-F | OH | Me, |
| 4'-methoxy | OH | Me, |
| 3',4'-dimethoxy | OH | Me, |
| 4'-i-propyl | OH | Me, |
| 4'-CN | OH | Me, |
| 4'-Br | OH | Me, |
| 4'-SMe | OH | Me, |
| 4'-$SO_2Me$ | OH | Me, |
| 3'-methoxy | OH | Me, |
| H | $EtCO_2$ | Me |

-continued
| $R^a$ | $R^b$ | $R^c$ |
|---|---|---|
| 4'-F | $EtCO_2$ | Me, |
| 3'-methoxy | $EtCO_2$ | Me, |
| 2'-Cl | $EtCO_2$ | Me, |
| 2',5'-dichloro | $EtCO_2$ | Me, and |
| 4'-methoxy | $EtCO_2$ | Me, |
including the stereoisomers thereof.
The most preferred compounds of Formula I are:
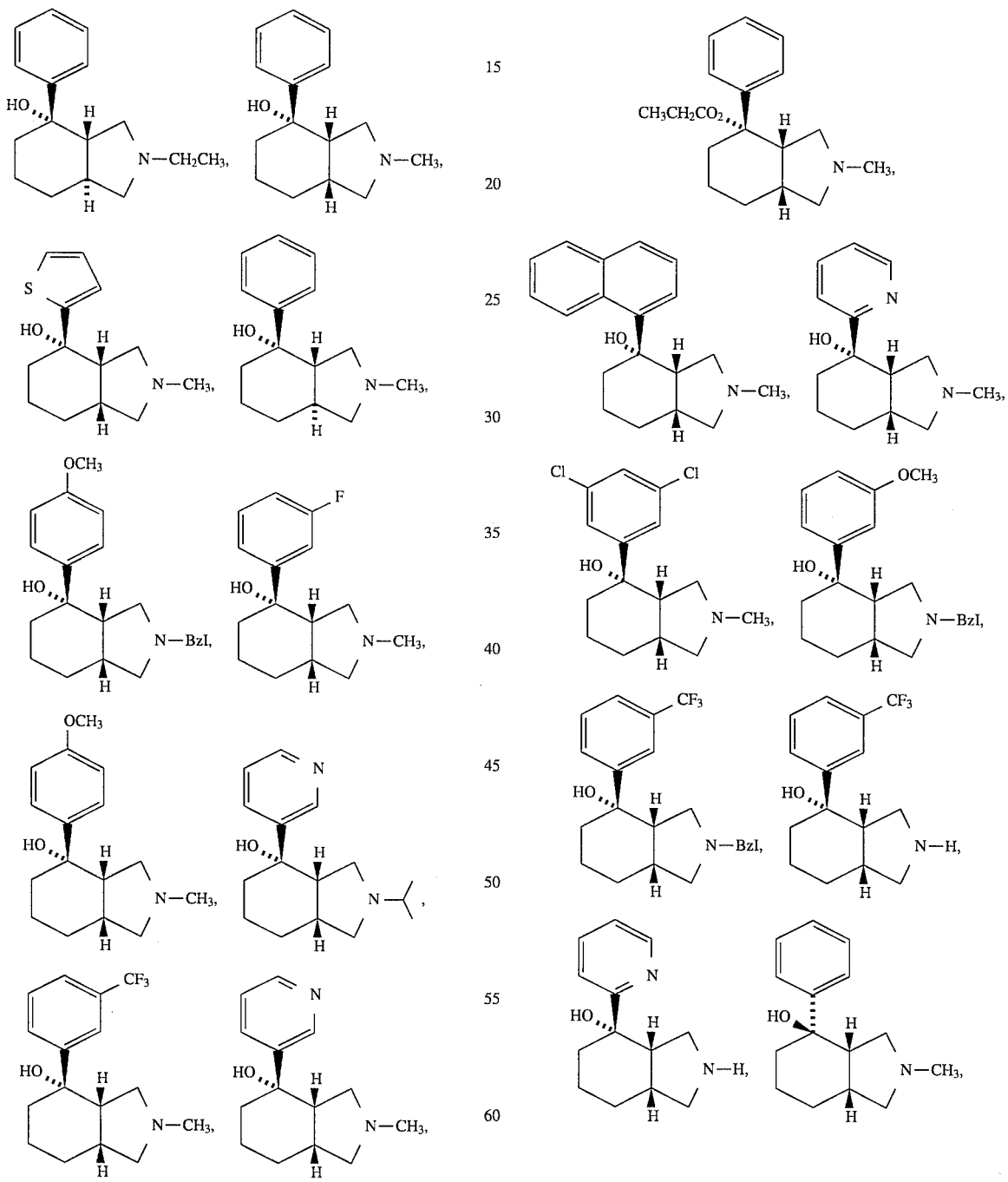

-continued

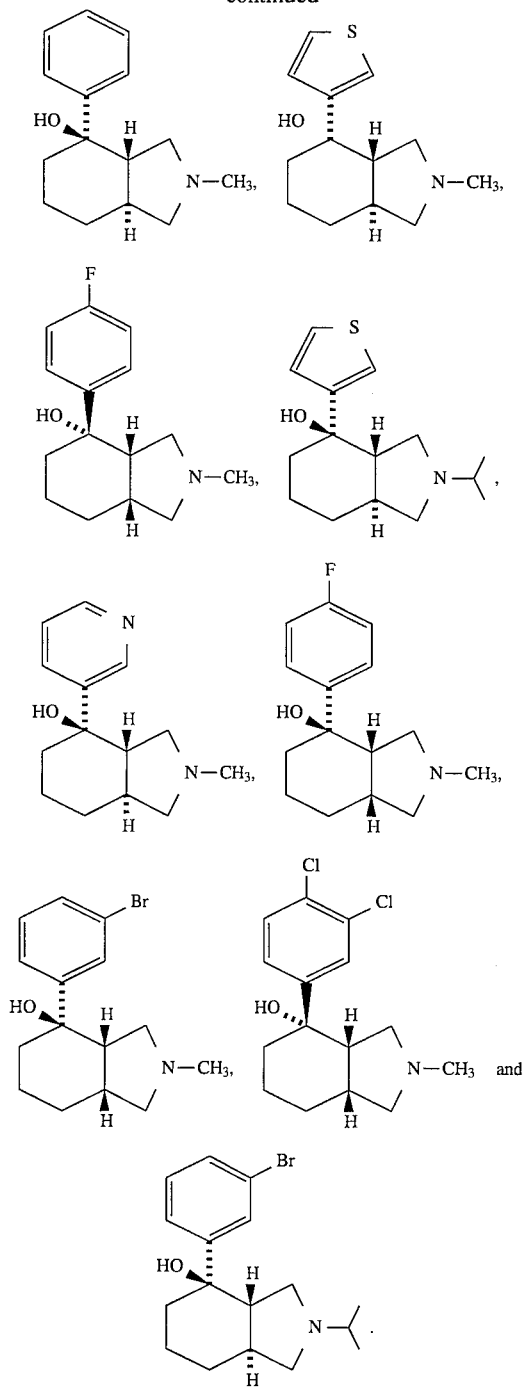

The activity of the compounds of the invention as analgesic agents may be demonstrated by the mouse acetylcholine-bromide induced constriction assay as described below:

Mouse Acetylcholine Bromide-Induced Abdominal Constriction Assay

The mouse acetylcholine-induced abdominal constiction assay, as described by Collier et al. in *Brit. J. Pharmacol. Chem. Ther.*, 32:295–310, 1968, with minor modifications was used to assess analgesic potency of the compounds of formula (I). The test drugs or appropriate vehicle were administered orally (p.o.) and 30 minutes later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten minute observation period for the occurrence of an abdominal constriction response (defined as a wave of constriction and elongation passing caudally along the abdominal wall, accompanied by a twisting of the trunk and followed by extension of the hind limbs). The percent inhibition of this response to a nociceptive stimulus (equated to % analgesia) was calculated as follows: The % Inhibition of response, i.e., % analgesia is equal to the difference between the No. of control animals response and the No. of drug-treated animals response times 100 divided by the No. of control animals responding.

At least 15 animals were used for control and in each of the drug treated groups. At least three doses were used to determine each dose response curve and $ED_{50}$ (that dose which would produce 50% analgesia). The $ED_{50}$ values and their 95% fiducial limits were determined by a computer assisted probit analysis.

TABLE 1

Mouse Acetylcholine-Bromide Induced Abdominal Constriction Assay

| Compound Number | % Inhibition | $ED_{50}$ |
|---|---|---|
| Cp-1 | | 7.3 po |
| Cp-2 | 30–40% @10 mpk/po | |
| Cp-3 | 46–93% @30 mpk/po | |
| Cp-4 | | 0.76 po |
| Cp-5 | | 16.6 po |
| Cp-6 | | 30.4 po |
| Cp-7 | | 5.38 po |
| Cp-8 | | 2.08 po |
| Cp-9 | | 15.4 po |
| Cp-10 | | 5.17 po |
| Cp-11 | | 1.36 po |
| Cp-12 | 90% @10 mpk/ko | |
| Cp-13 | 75% @30 mpk/sc | |
| Cp-14 | 50% @30 mpk/po | |
| Cp-15 | 90% @10 mpk/po | |
| Cp-16 | | 3.9 po |
| Cp-18 | 71% @30 mpk/po | |
| Cp-19 | | 4.2 po |
| Cp-20 | | 10.7 po |

Based on the above results, invention compounds of formula (I) may be used to treat mild to moderately severe pain in warm-blooded animals such as humans in a manner similar to the use of meperidine hydrochloride by administration of an analgesically effective dose. The dosage range would be from about 10 to 3000 mg, in particular about 25 to 1000 mg or about 100 or 500 mg, of active ingredient 1 to 4 times per day for an average (70 kg) human although it is apparent that activity of individual compounds of the invention will vary as will the pain being treated. Pharmaceutical compositions of the invention comprise the formula (I) compounds as defined above, particularly in admixture with a pharmaceutically-acceptable carrier.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intra muscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The pharmaceutically acceptable salts referred to above generally take a form in which the nitrogen of the core ring and/or possibly a nitrogen of a substituent is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic or saccharic.

The following examples illustrate the invention in greater detail, but are not meant to limit its scope. The analytical data for all examples are the experimental values.

Procedure A

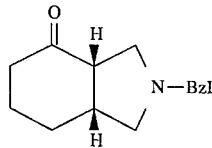

aa

2-Benzyl-3aα,7aα-Octahydroisoindol-4-One

A mixture of N-butoxymethyl-1-benzyl)trimethylsilanylmethylamine (160 g, 0.57 mol) prepared as described in Hosomi, et al, *Chemistry Letters* 1984, 17–1120), 2-cyclohex-2-enone (48 g, 0.5 mol), dry CH2Cl2 (640 mL) and TFA/CH$_2$Cl$_2$ (28.5 mL) was heated at reflux for 2 h under argon. K$_2$CO$_3$ was added to the mixture followed by a portion of water. The resulting organic layer was separated, washed with brine, dried (K$_2$CO$_3$) and concentrated in vacuo. The residue was purified by column chromatography. An oxalate salt was prepared in EtOH and recrystallized from EtOH to give the title compound: mp 129°–130° C. H$^1$ NMR (CDCl$_3$) d 7.3, 5H m; 3.6 2H s; 2.7–2.9 4H m; 2.35 2H t; 2.25 2H m; 1.9 3H m; 1.4 1H m. MS 229 Cl/CH$_3$.

Anal. Calc'd for $C_{15}H_{19}NO.C_2H_2O_4$: C, 63.99; H, 6.63; N, 4.39 Found: C, 63.71; H, 6.62; N, 4.24

Procedure B

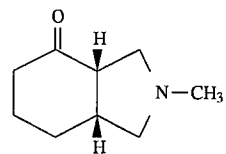

bb

2-Methyl-3aα,7aα-Octahydroisoindol-4-One

A mixture of 2-benzyl-2-perhydroisoindol-4-one (2.5 g, 0.011 mol), ethyl acetate (30 mL) and methyl trifluorosulfonate (2.1 g, 0.013 mol) was stirred overnight under argon. Methyl trifluorosulfonate (0.2 g, 1.2 mmol) was added and the resulting mixture was stirred for 4 h. Another portion of methyl trifluorosulfonate (1.0 g, 6.1 mmol) was added and the mixture was stirred for an additional 72 h. The resulting precipitate was washed with Et$_2$O and dissolved in EtOH. The solution was placed in a parr bottle and 10% Pd/C (0.4 g) was added to it. The mixture was shaken under an atmosphere of H$_2$ for 1.5 h and filtered. The filtrate was concentrated in vacuo and partitioned between Et$_2$O and 3N NaOH. The organic layer was dried (K$_2$CO$_3$), concentrated in vacuo and purified by bulb to bulb distillation to give the title compound as an oil.

EXAMPLE 1

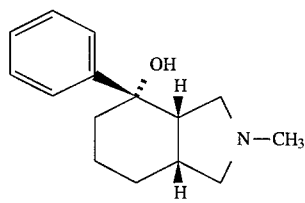

Cp-16

4β-Hydroxy-4-Phenyl-2-Methyl-3aα,7aα-Octahydroisoindole

Phenyl lithium (1.8M in Et$_2$O, 54.7 mL, 0.098 mol) was added dropwise to a cooled (0° C.) solution of 2-methyl-3aα,7aα-octahydroisoindole (5.0 g, 0.33 mol) and Et$_2$O (100 mL). The cooling bath was removed and the reaction mixture was allowed to warm up to room temperature, stirred for 1 h and poured into water. The resulting organic layer was washed with successive portions of water and brine, dried (K$_2$CO$_3$) and concentrated in vacuo. The residue was purified by column chromatography using CH$_2$Cl$_2$:MeOH:NH$_4$OH (80:20:2) as an eluent and converted to the fumarate salt in isopropanol to give the title compound as a solid: mp 180°–182° C.

Anal calcd for $C_{15}H_{21}NO/C_4H_4O_4$: C,65.69; H, 7.25; N, 4.03 Found: C, 65.37; H, 7.27; N, 3.79

PROCEDURE C

The following general procedure was used to synthesize the compounds listed in tables 2 and 3.

A solution of an appropriately substituted aryl organometallic derivative, (3 equivalents) was added dropwise to a cooled (0° C.) solution of the appropriately 2-substituted-3aα, 7aα-octahydroisoindol-4-one derivative (1 equivalent) and an inert solvent (100 mL/0.33 mol). The cooling bath was removed and the reaction mixture was allowed to warm up to room temperature, stirred for 1 h and poured into water, The resulting organic layer was washed with successive portions of water and brine, dried (K$_2$CO$_3$) and concentrated in vacuo. The residue was purified by column chromatography and recrystallization. This compound may be used as is or converted to a suitable organic or inorganic salt.

at 0.001 mm Hg to give the title compound as a clear oil between 38°–45° C.

TABLE 2

| Cp-# | | mp °C. | Empirical Formula | C | H | N |
|---|---|---|---|---|---|---|
| Cp-1 | thien-2-yl | 199–201 | $C_{13}H_{19}NOS.0.75\ C_4H_4O_4$ | 59.36 | 7.06 | 4.32 |
| Cp-3 | 4-OCH$_3$-phenyl | 173–174 | $C_{16}H_{23}NO_2.C_4H_4O_4$ | 63.73 | 7.30 | 3.69 |
| Cp-4 | 4-F-phenyl | 192–193 | $C_{15}H_{20}NO.C_4H_4O_4$ | 62.14 | 6.61 | 3.77 |
| Cp-5 | 1-napthyl | 179–180 | $C_{19}H_{23}NO.0.75\ C_4H_4O_4$ | 71.58 | 7.42 | 3.76 |
| Cp-6 | pyridin-3-yl | 75–80 | $C_{14}H_{20}N_2O$ | 72.26 | 8.72 | 11.99 |
| Cp-7 | 3-F-phenyl | 163–165 | $C_{15}H_{20}FNO.C_4H_4O_4$ | 62.34 | 6.66 | 3.85 |
| Cp-8 | 3-CF$_3$-phenyl | 188–189 | $C_{16}H_{20}F_3NO.C_4H_4O_4$ | 57.83 | 5.82 | 3.37 |
| Cp-9 | pyridin-2-yl | 66–70 | $C_{14}H_{20}N_2O$ | 72.46 | 8.72 | 12.06 |
| Cp-11 | 2,4-diCl-phenyl | 169–171 | $C_{15}H_{19}Cl_2NO.C_4H_4O_4$ | 54.85 | 5.80 | 3.16 |

TABLE 3

| Cp-# | $R^{a1}$ | $R^c$ | mp °C. | Empirical Formula | C | H | N |
|---|---|---|---|---|---|---|---|
| Cp-13 | 3-OCH$_3$ | Bzl | 183–185 | $C_{22}H_{27}NO_2.HCl.0.20\ H_2O$ | 69.72 | 7.44 | 3.74 |
| Cp-18 | 3-CF3 | Bzl | 170–172 | $C_{22}H_{24}F_3NO.C_4H_4O_4$ | 63.50 | 5.67 | 2.81 |
| Cp-19 | 3-CF3 | H | 168–170 | $C_{15}H_{18}F_3NO.C_4H_4O_4$ | 56.56 | 5.41 | 3.41 |
| Cp-20 | 4-CF3 | Bzl | 143–45 | $C_{22}H_{24}F_3NO.C_4H_4O_4.0.25\ H_2O$ | 62.9 | 6.01 | 2.72 |

PROCEDURE D

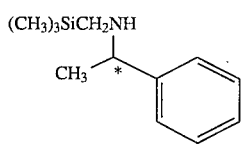

(R)-[(1-Phenylethyl)Trimethylsilanylmethyl]Amine

Chloromethyl(trimethylsilyl)methylamine (25 g, 0.166 mol) was treated under reflux with (R)-(+)-α-methylbenzylamine (78.5 mL, 0.61 mol) for 6 h. After cooling 100 mL of 15% KOH was added. The resulting solution was stirred before extracting twice with diethyl ether. The organics were combined and washed with brine and dried (K$_2$CO$_3$). The solvent was removed in vacuo and the residue was distilled Mass spectrum (CH$_4$Cl) e/z 208 (M+1). NMR (CDCl$_3$) δ7.3–7.2 (Ar, 5 H); 3.4 (q, 1 H); 1.85 (q, 2 H); 1.3 (d, 3 H).

Anal Calcd for C$_{12}$H$_{21}$NSi: C, 69.50; H, 10.21; N, 6.75. Found: C, 69.20; H,10.25, N, 6.78.

PROCEDURE E

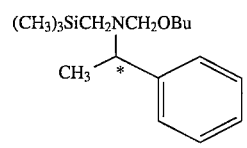

N-(Butoxymethyl-(R)-1-Phenylethyl)Trimethylsilanylmethylamine

A mixture of (12.7 mL, 0.14 mol) of 1-butanol and 9.4 mL of 37%aq formaldehyde was cooled in a ice bath. [((R)-1- phenylethyl)trimethylsilanylmethyl]amine (24.0 g, 12 mol) was added dropwise. The reaction was stirred in an ice bath for 8 h after which K₂CO₃ was added. Diethyl ether was added and the organics were separated off, washed with brine and dried (K₂CO₃). The solvent was evaporated in vacuo. A bulb-to-bulb distillation of the residue at 70°–85° C. (0.001 mmHg) gave 19.3 g of a clear oil. NMR (CDCl₃) δ7.4–7.1 (Ar, 5 H); 4.2 (m, 1 H); 4.1–3.9 (dd,m, 2 H); 3.2 (m, 2 H); 2.1 (q, 3 H); 1.5 (m, 2 H); 1.3 (d,m, 4 H); 0.9 (t, 3 H).

PROCEDURE F

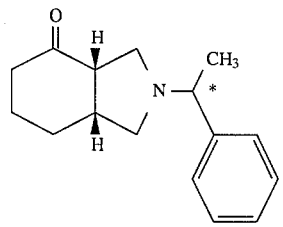

2-((R)-1-Phenylethyl)-3aα,7aα-Octahydroisoindol-4-One

A mixture of (R)-N-(butoxymethyl-1-phenylethyl)trimethylsilanylmethylamine (5.0 g, 0.017 mol), methylene chloride(25 mL), 2-cyclohexen-1-one (1.25 mL, 1.29 mol) and 1% trifluoroacetic acid (TFA, 15 drops) in methylene chloride was treated under reflux for 3 h. K₂CO₃ was added and stirred for one hour. Water was added and the organics were separated off. The organics were washed with water, brine and dried (K₂CO₃). The solvent was removed in vacuo. The residue was flash chromatographed on silica gel (6:1 hexane:acetone) to give 2.87 g of product. Mass spectrum (CH₄—Cl) m/z 228 (M–15). NMR (CDCl₃) δ 7.2 (Ar, 5 H); 3.2 (q, 1 H); 3.0–2.6 (m, 5 H); 2.3 (t, 2 H); 2.1 (m, 1 H), 1.8 (m, 3 H); 1.4–1.2 (dd,m, 4 H).

PROCEDURE G

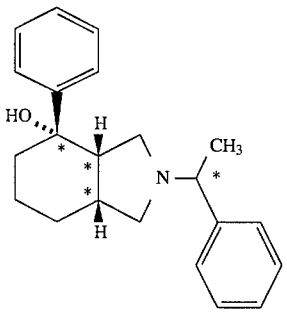

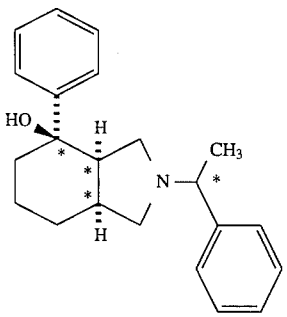

4β-Hydroxy-2-((R)- 1-Phenylethyl)-4-Phenyl-3aα-7aα-Octahydroisoindole

A solution of 1.8M phenyllithium in cyclohexane/diethyl ether was cooled to –78° C. A solution of 3aα,7aα-2-[(R)-α-methyl(phenylmethyl)]- 1,3,3a,5,6,7-hexahydro-4H-isoindol-4-one (4.79 g, 0.020 mol)in diethyl ether (100 mL) was added dropwise. The reaction was stirred for 1.5 h then poured into water. The organics were separated off and the aqueous layer was extracted with diethyl ether. The organics were combined washed with water, brine and dried (K₂CO₃). The solvent was removed in vacuo. The diastereomers were separated on a Waters Prep 500 HPLC using silica gel columns and 5:1 hexane:acetone as eluant. Diastereomer A (+) mp (HCl) 145°–147° C. Mass spectrum (CH₄—Cl) m/z 322 (M+1). NMR (CDCl₃) δ7.5–7.0 (Ar, 10 H); 3.35 (q, 1 H); 3.1 (m, 1 H); 2.7–2.5 (m, 2 H); 2.45 (d, 1 H); 2.35 (m, 1H); 2.05 (m, 3 H); 1.7 (m,4 H); 1.4 (d, 3 H). Diastereomer B (–) mp (HCl) 146°–149° C. Mass spectrum (CH₄—Cl) m/z 322 (m+1). NMR (CDCl₃) δ7.5–7.0 (Ar, 10 H); 3.4 (q, 1 H); 3.05 (d, 1 H); 2.6 (m, 1 H); 2.5 (m, 1 H); 2.3 (m, 2 H); 2.1–1.7 (m, 3 H); 1.65 (m, 3 H); 1.6 (m, 1 H); 1.4 (d, 3 H).

EXAMPLE 2

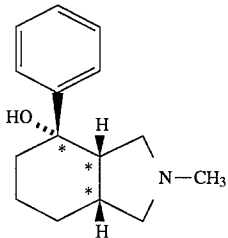

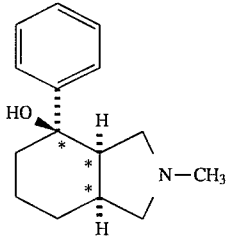

(+)-4β-Hydroxy-2-Methyl-4-phenyl-3aα,7aα-octahydroisoindole-Cp-15

4β-Hydroxy-2-((R)-1-phenylethyl)-4-phenyl-3aα-7aα -octahydroisoindole (3.5 g, 0.011 mol) was combined with (1.3 mL, 0.012 mol) methyl triflate in 80 mL of methylcyclohexane and stirred for 3.5 h. The solid was filtered off and placed into a Parr jar over 2.0 g 10% palladium on carbon and 150 mL ethanol. The mixture was shaken on a Parr shaker under 50 psi hydrogen for 1 h. The catalysts was filtered off and the filtrate was evaporated in vacuo. The residue was flashed chromatographed on silica gel with 80:20:1.0 methylene chloride:methanol:ammonium hydroxide. The product was dissolved in methylene chloride and washed with 3N NaOH, water, brine and dried (K₂CO₃). This was flashed chromatographed on silica gel (80:20:2 CH₂Cl₂:MeOH: NH₄OH). The resulting oil was converted to the cyclohexanesulfamic acid salt in acetonitrile to give 20 mg of product. mp. 127°–129° C. [α]=–0.80. Mass spectrum (CH₄—Cl) m/z 232 (M+1). NMR for free base (CDCl₃) δ 7.6–7.1 (Ar, 5 H); 3.0 (t, 1 H); 2.7 (d, 1 H), 2.6 (m, 1 H); 2.4 (m, 1 H); 2.3 (s, 3 H); 2.15 (m, 2 H); 2.0 (m, 1 H); 1.6 (m, 4 H); 1.4 (m, 1 H).

Anal calcd for $C_{15}H_{21}$ NO/1.3 $C_6H_{13}NO_3S$: C, 58.98; H, 8.23; N, 6.94. Found: C, 59.03; H, 8.34; N, 7.01.

(−)-4β-Hydroxy-2-Methyl-4-Phenyl-3aα,7aα-Octahydroisoindole-Cp-12

(−)-4β- Hydroxy-2-(R)-α-methylbenzyl-4-phenyl-3aα-7aα-octahydroisoindole (2.68 g, 0.008 mol) was combined with methyl triflate (1.0 mL, 0.008 mol) in 80 mL of methylcyclohexane, 1.3 g 10% palladium on carbon and 125 mL ethanol. The mixture was shaken on a Parr shaker under 50 psi hydrogen for 1.5 h. The catalysts was filtered off and the filtrate was evaporated in vacuo. The residue was flashed chromatographed twice on silica gel with 80:20:1.0 methylene chloride:methanol:ammonium hydroxide. The product was dissolved in methylene chloride and filtered. The filtrate was evaporated in vacuo. The resulting oil was converted to the cyclohexanesulfamic acid salt in acetonitrile to give 20 mg of product. mp. 128°–130° C. mass spectrum (CH$_4$—Cl) m/z 232 (M+1). NMR for free base (CDCl$_3$) δ 7.6–7.1 (Ar, 5 H); 3.0 (t, 1 H); 2.7 (d, 1 H), 2.6 (m, 1 H); 2.4 (m, 1H); 2.3 (s, 3 H); 2.15 (m, 2 H); 2.0 (m, 1 H); 1.6 (m, 4 H); 1.4 (m, 1 H).

Anal calcd for $C_{15}H_{21}NO/C_6H_{13}NO_3S$: C, 61.43 H, 8.35; N, 6.82. Found: C, 61.42; H, 8.34; N, 6.86

EXAMPLE 3

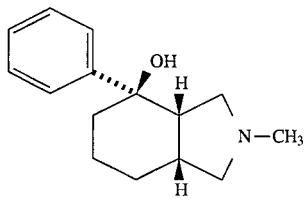

Cp-17

4β-Hydroxy-2-Methyl-4α-Phenyl-3aα7aα-Octahydroisoindole

4β-Hydroxy-2-methyl-4-phenyl-3aα,7aα-octahydroisoindole (1.8 g, 0.008 mol) was combined with 16 mL of 2N H$_2$SO$_4$ and heated to 80° C. overnight. The reaction was made basic by NaOH addition and the resulting solution was extracted twice with diethyl ether. The organic layers were combined, washed with brine and dried (Na$_2$SO$_4$). The solvent was removed in vacuo and the resulting residue was passed through a silica gel column on a Waters Prep 500 HPLC to give 0.4 g of a glass. $^{13}$CNMR δ 147.4 (Ph, C-1 ), 128.4 (Ph), 127.4 (Ph), 124.8 (Ph), 72.9 (C-4), 62.9 (CH$_2$-3), 55.67 (CH2-1), 49.7 (CH-3a), 43.5 (CH-7a), 37.0 (CH$_3$-N), 31.5 (CH$_2$-5), 27.4 (CH$_2$-7), 20.1 (CH$_2$-6). HNMR (CDCl$_3$) δ7.4 (Ar, 2 h), 7.25–7.0 (Ar, 3 H), 2.65 (m, 1 H), 2.4–2.15 (m, 4 H), 2.1 (s, 3 H), 2.05–2.0 (m, 1 H), 1.7 (m, 1 H), 1.55 (m, 3 H), 1.3–1.1 (m, 1 H). Mass spectrum, exact mass calcd for $C_{15}H_{21}NO$: 232.1701. Found: 232.1726.

PROCEDURE H.

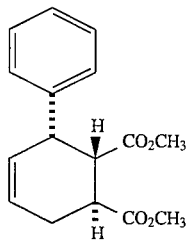

Dimethyl (1α,2β,3β)-3-Phenylcyclohex-4-Ene-1,2-Dicarboxylate

A mixture of trans-1-phenyl-1,3-butadiene (54 g, 0.414 mol) and dimethyl fumarate (59.85 g, 0.414 mol) in 270 mL ethylene glycol was heated at 95° C. for 16 h. It was poured into H$_2$O and extracted with Et$_2$O. The Et$_2$O extract was washed with brine, dried (MgSO$_4$) and concentrated to dryness. The starting materials were removed by bulb to bulb distillation (30°–100° C.,0.05 Torr). The residue was crystallized from methyl t-butyl ether and recrystallized twice more from the same solvent to give 20.0 g (17.6% yield) of the title compound as a white solid: mp 142°–143° C.; $^1$H NMR (CDCl$_3$) d 7.26 (m, 3H), 7.13 (dd, 2H), 6.0 (m, 1H), 5.8 (m, 1H), 3.95 (t, 1H), 3.65 (s, 3H), 3.45 (s, 3H), 3.25 (m, 1H), 3.0 (m, 1H), 2.6 (m, 1H), 2.25 (m, 1H).

Anal. calcd for $C_{16}H_{18}O_4$: C, 70.06; H, 6.61. Found: C, 70.03; H, 6.66.

PROCEDURE I

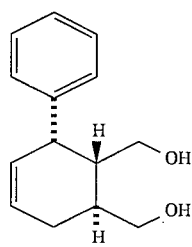

(1α,5β,6α)-(6-Hydroxymethyl-2-Phenylcyclohex-3-Enyl)Methanol

A soluton of dimethyl (1α,2β,3β)-3-phenylcyclohex-3-ene-1,2-dicarboxylate (20.0 g, 0.073 mol) in 250 mL of Et$_2$O was added dropwise to a suspension of lithium aluminum hydride (13.85 g, 0.365 mol)in 150 mL of Et20 under argon. The mixture was stirred for 16 h. Samples of H$_2$O (19 mL), 3N NaOH (57 mL), and H$_2$O (19 mL) were added dropwise with cooling. The solid was removed by filtration. The filtrate was concentrated to dryness and the residue was crystallized from EtOAc to give 11.8 mg of the title compound as a white solid.

Anal. calcd for $C_{14}H_{18}O_2$: C,77.03; H, 8.31 Found: C, 76.93; H, 8.41.

PROCEDURE J

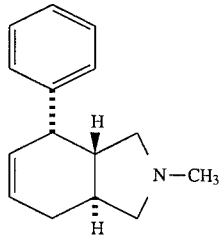

2-Methyl-4β-Phenyl-2,3,3aα,4,7,7aβ-Hexahydro-1H-Isoindole Monofumarate

A solution of (1α,2β,6α)-(6-hydroxymethyl-2-phenylcyclohexene)methanol (11.65 g, 0.053 mol) and triethylamine (16.34 mL, 0.117 mol) in 120 mL of CH$_2$Cl$_2$ was cooled to 0° C. and methanesulfonyl chloride (9.09 mL, 0.117 mol) was added dropwise so that the temperature did not exceed 8° C. The mixture was stirred for 2 h, then washed with H$_2$O, dilute HCl and NaHCO$_3$ solution. The solution was dried (MgSO₄) and evaporated to dryness. The residue was taken up in 500 mL of EtOH, methylamine (13.8 g, 0.44 mol) was added and the resulting solution was heated at 95° C. for 16 h. The solvent was evaporated and the residue partitioned between NaOH solution and CH₂Cl₂. The organic solution was dried (K₂CO₃) and the solvent was evaporated. A fumarate salt was prepared (2-PrOH solvent) to afford 8.7 g (50% yield) of the title compound as a white solid: mp 153°–155° C.; ¹H NMR (CDCL₃) d 7.3 (m, 3H), 7.2 (dd, 2H), 6.4 (s, 2H), 6.0 (m, 1H), 5.72 (m, 1H), 3.72 (t, 1H), 3.35–3.20 (m, 2H), 2.87 (t, 1H), 2.55 (s, 1H), 2.4–2.2 (m, 2H), 1.9 (m, 3H).

Anal. calcd for $C_{15}H_{19}N$—$C_4H_4O_4$: C, 69.28; H,7.04; N, 4.25 Found: C, 69.00; H, 7.22; N, 4.14.

PROCEDURE K

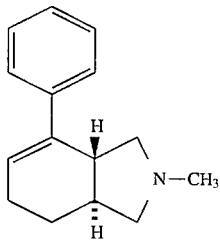

2-Methyl-4-Phenyl-2,3,3aα,6,7,7aβ-Hexahydro-1H-Isoindole Monofumarate

A sample of 2-methyl-4b-phenyl-2,3,3aα, 4,7,7aβ-hexahydro-1H-isoindole (5.3 g, 0.0248 mol)in 25 mL THF was stirred under argon and of potassium t-butoxide (2.79 g, 0.024 mol) was added. The mixture was heated under reflux for 16 h. It was partitioned between Et₂O and H₂O. The organic layer was washed with brine, dried and concentrated to dryness. The residual oil was chromatographed on SiO₂ on a Waters "Prep 500"HPLC, eluting with 5%NH₄OH in 2-PrOH. The trailing spot was collected and converted to the fumarate salt in 2-PrOH to give the title compound as a white solid: mp 142°– 145° C.; ¹H NMR (DMSO-d₆)d 7.35 (m, 5H), 6.5 (s, 2H), 5.88 (dd, 1H), 3.45 (m, 1H), 3.1 (m, 1H), 2.88 (t, 1H), 2.7 (s, 3H), 2.55 (m, 1H), 2.45 (m, 1H), 2.3 (m, 1H), 2.1 (m, 1H) 2.0 (m, 1H), 1.5 (m, 1H). Mass spectrum, exact mass calcd for $C_{15}H_{19}N$: 213.1518. Found:213.1572.

EXAMPLE 4

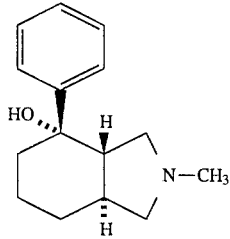

Cp-2

4β-Hydroxy-2-Methyl-4a-Phenyl-3aα, 7aβ-Octahydro-1H-Isoindole Monofumarate

A solution of 2-methyl-4-phenyl-2,3,3aα,6,7,7aβ-hexahydro-1H-isoindole (0.78 g, 3.66 mmol) in 12 mL of CHCl₃ was treated with 85%m-chloroperbenzoic acid (2.22 g, 11 mmol). The mixture was stirred for 16 h. It was washed with NaSO₃ solution, NaHCO₃ solution, dried (K₂CO₃) and concentrated to dryness. The resulting crude epoxy-N-oxide was taken up in 10 mL of THF and the solution was added dropwise to lithium aluminum hydride (0.68 g, 17.9 mmol)in 10 mL of THF. The mixture was heated under reflux for 3 h. It was cooled and treated successively with 0.7 mL H₂O, 2.1 mL 3N NaOH and 0.7 mL H₂O. The solid was removed by filtration. The filtrate was evaporated and the residue was chromatographed on SiO₂ using a Waters "Prep 500" HPLC with CH₂Cl₂:CH₃OH:NH₄OH, 90:10:1 as eluant. The first peak which emerged was converted to its fumarate salt (2-PrOH) to afford the title compound as a white solid: mp 203°–204° C.; ¹H NMR (DMSO-d₆) d 7.5 (dd, 2H), 7.35 (t, 2H), 7.26 (t, 1H), 6.46 (s, 2H), 3.4 (m, 1H), 2.9 (t, 1H), 2.7 (m, 1H), 2.65 (s, 3H), 2.3 (m, 2H), 1.84 (d,1H), 1,65 (m, 4H), 1.20 (m, 1H).

Anal. calcd for $C_{15}H_{21}NO$—$C_4H_4O_4$: C, 65.69; H, 7.25, N, 4.03 Found: C, 65.48; H, 7.33; N, 4.32.

EXAMPLE 5

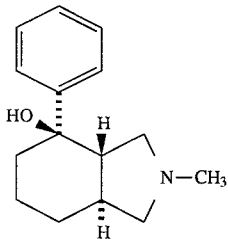

Cp-14

4α-Hydroxy-2-Methyl-4-Phenyl-3aα,7aβ-Octahydro-1H-Isoindole

Further elution of the chromatography column from the previous example (CH₂Cl₂:CH₃OH:NH₄OH, 80:20:2) gave a second peak. The solvent was evaporated and the residue crystallized from methyl t-butyl ether to give the title compound as a white solid: mp 113°–114° C.; ¹H NMR (CDCl₃) d 7.4–7.2 (m, 5H), 3.9 (br s, 1H), 2.9 (m, 1H), 2.75 (m, 2H), 2.5 (m, 2H), 2.42 (s, 3H) 2.39 (m, 1H), 2.1 (m, 1H), 1.8–1.5 (m, 4H), 1.4 (br s, 1H).

Anal. calcd for $C_{15}H_{21}NO$: C, 77.88; H, 9.15; N, 6.05 Found: C, 77.76; H, 9.19; N, 5.94.

What is claimed is:

1. A compound having analgesic activity of the formula:

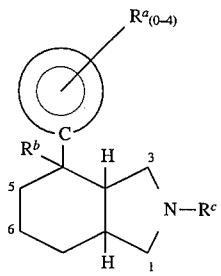

I including the purified stereoisomers and pharmaceutically acceptable salts thereof, wherein

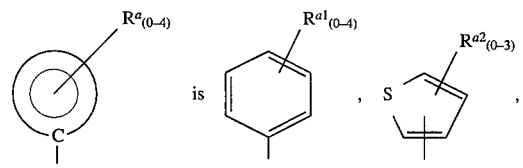

-continued

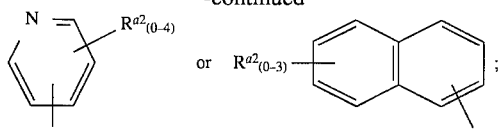

$R^{a1}$ is selected from the group consisting of hydrogen, halogen, $C_{1-4}$alkyl, substituted $C_{1-4}$alkyl (wherein the substituent is $C_{1-4}$alkoxy, hydroxy or perhalo), $C_{1-4}$alkoxy, substituted $C_{1-4}$alkoxy (wherein the substituent is perfluoro), $C_{1-4}$alkylthio, cyano, $diC_{1-4}$alkylamino, $C_{1-4}$alkylsulfonyl, $C_{1-4}$alkylsulfinyl, phenyl, phenylthio and carboxy;

$R^{a2}$ is selected from the group consisting of halogen or $C_{1-4}$alkyl;

$R^b$ is hydroxy or $C_{1-5}$ alkylcarbonyloxy;

$R^c$ is selected from the group consisting of hydrogen, $C_{1-4}$ alkyl, substituted $C_{1-4}$alkyl (wherein the substituent is one or two phenyl groups or $diC_{1-4}$alkylamino), $C_{1-4}$alkenyl and benzyl.

2. The compound of claim 1 having the formula:

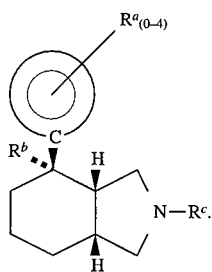

3. The compound of claim 1 having the formula:

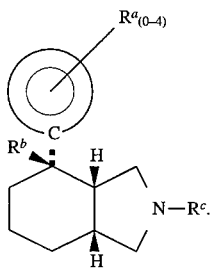

4. The compound of claim 1 having the formula:

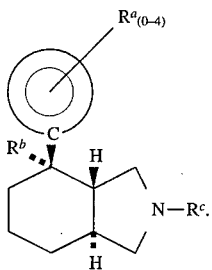

5. The compound of claim 1 having the formula:

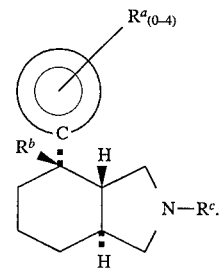

6. The compound of claim 1 wherein

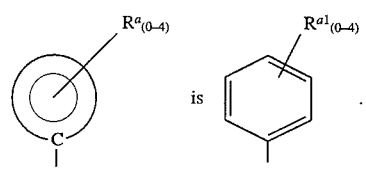

7. The compound of claim 1 which is a salt of an organic or inorganic acid selected from the group consisting of hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic or saccharic.

8. The compound of claim 1 wherein $R^{a1}$ is selected from the group consisting of bromine, chlorine, fluorine, methyl, ethyl, n-propyl, i-propyl, t-butyl, methoxymethyl, ethoxyethyl, hydroxymethyl, hydroxyethyl, hydroxypropyl, trifluoromethyl, trichloromethyl, methoxy, ethoxy, t-butoxy, trifluoromethoxy, methylthio, ethylthio, n-propylthio, cyano, dimethylamino, diethylamino, methylethylamino, methylsulfonyl, ethylsulfonyl, n-propylsulfonyl, methylsulfinyl, ethylsulfinyl, n-propylsulfinyl, phenyl, phenylthio and carboxy.

9. The compound of claim 1 wherein $R^{a2}$ is selected from the group consisting of bromine, chlorine, fluorine, methyl, ethyl, n-propyl, i-propyl or t-butyl.

10. The compound of claim 1 wherein $R^b$ is selected from the group consisting of hydroxy and ethylcarbonyloxy.

11. The compound of claim 1 wherein $R^c$ is selected from the group consisting of hydrogen, methyl, ethyl, n-propyl, i-propyl, t-butyl, dimethylaminomethyl, dimethylaminoethyl, dimethylaminopropyl, diethylaminomethyl, diethylaminoethyl and allyl.

12. The compound of claim 1 having the general formula:

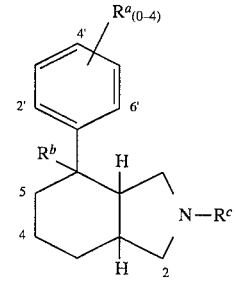

wherein $R^a$, $R^b$ and $R^c$ are simultaneously selected from the group consisting of the groups:

| $R^a$ | $R^b$ | $R^c$ |
|---|---|---|
| 4'-F | OH | Me, |
| 3'-methoxy | OH | Me, |
| 3'-methoxy | OH | H, |
| 3'-CF$_3$ | OH | Me, |
| 3'-methoxy | OH | H, |
| 2',3'-dimethoxy | OH | Me, |
| 3',4'-dichloro | OH | Me, |
| — | OH | Me, |
| 4'-CF$_3$ | OH | Me, |
| 3'-CF$_3$ | OH | n-butyl, |
| 4'-Cl | OH | Me, |
| 2'-Cl | OH | Me, |
| 2',5'-dichloro | OH | Me, |
| 4'-F | OH | Me, |
| 4'-methoxy | OH | Me, |
| 3',4'-dimethoxy | OH | Me, |
| 4'-i-propyl | OH | Me, |
| 4'-CN | OH | Me, |
| 4'-Br | OH | Me, |
| 4'-SMe | OH | Me, |
| 4'-SO$_2$Me | OH | Me, |
| 3'-methoxy | OH | Me, |
| H | EtCO$_2$ | Me |
| 4'-F | EtCO$_2$ | Me, |
| 3'-methoxy | EtCO$_2$ | Me, |
| 2'-Cl | EtCO$_2$ | Me, |
| 2',5'-dichloro | EtCO$_2$ | Me, and |
| 4'-methoxy | EtCO$_2$ | Me, | including the stereoisomers thereof.

13. A compound selected from the group consisting of:

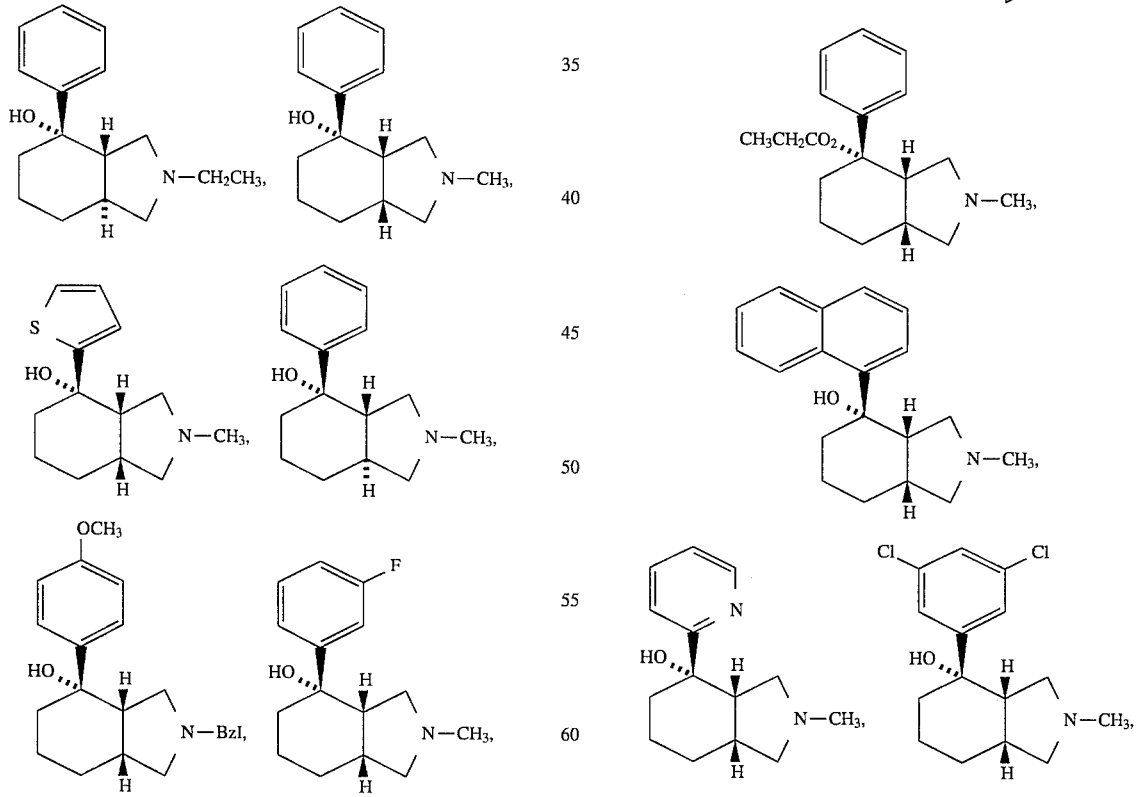

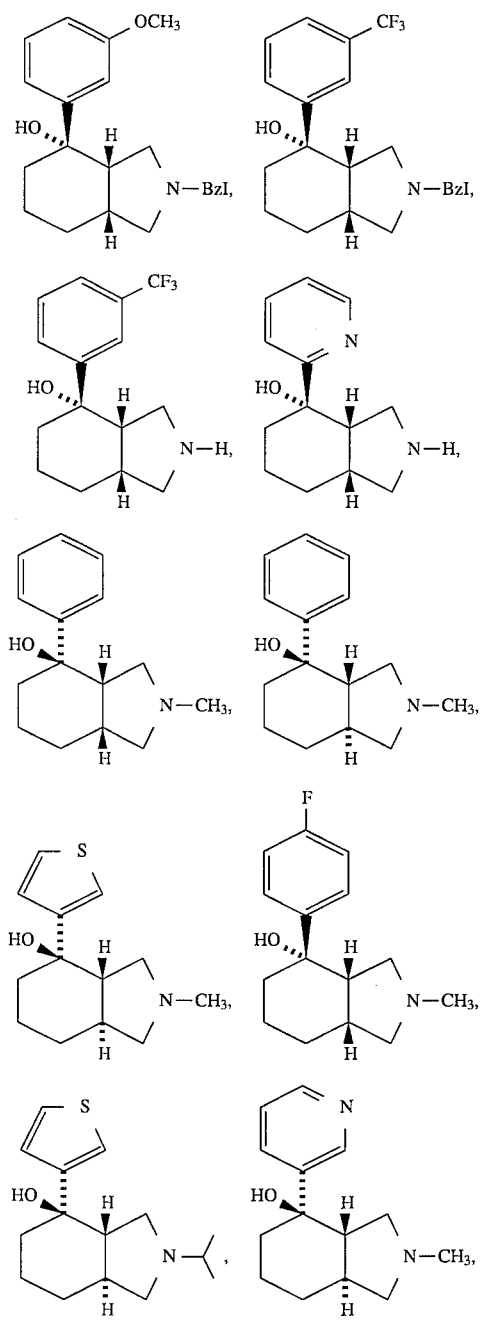

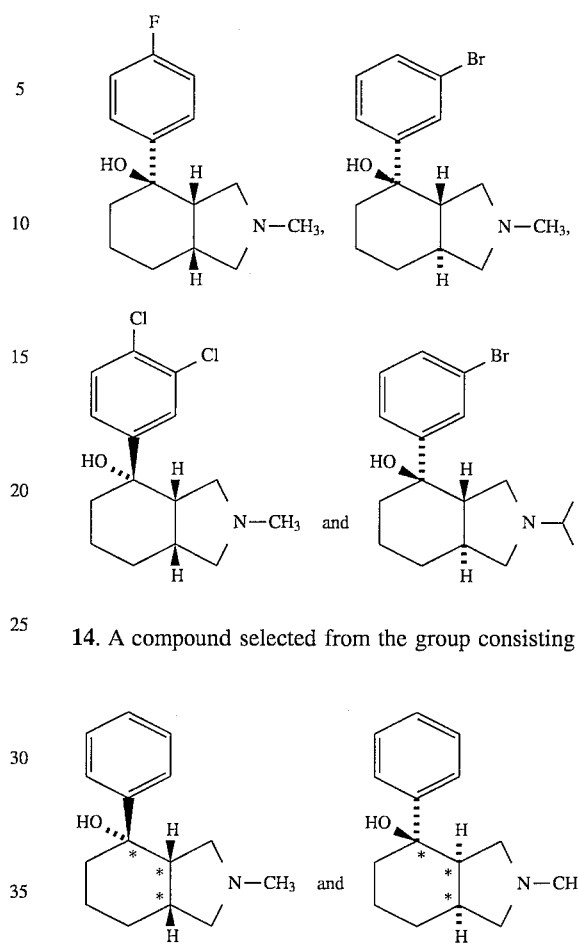

14. A compound selected from the group consisting of:

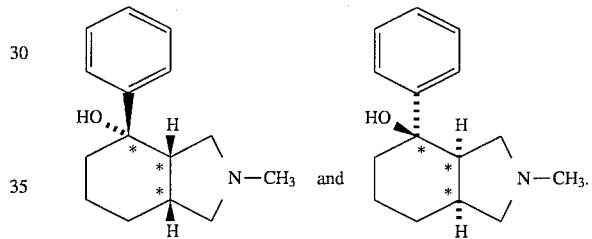

15. A pharmaceutical composition effective as an analgesic in mammals comprising a pharmaceutically acceptable carrier and an effective amount of the compound of claim 1.

16. A method for inducing an analgesic effect in mammals comprising the step of administering an effective amount of the compound of claim 1 in admixture with a pharmaceutically acceptable carrier.

* * * * *